United States Patent [19]

Frainier et al.

[11] 4,251,396

[45] Feb. 17, 1981

[54] COPPER CHROMITE CATALYST FOR PREPARATION OF FURFURYL ALCOHOL FROM FURFURAL

[75] Inventors: Leo J. Frainier; Herman H. Fineberg,

[73] Assignee: Ashland Oil, Inc., Ashland, Ky.

[21] Appl. No.: 15,574

[22] Filed: Feb. 26, 1979

[51] Int. Cl.$^3$ .................. B01J 23/26; B01J 23/72
[52] U.S. Cl. .................. 252/467; 260/347.8
[58] Field of Search .......... 252/467; 260/347.8; 423/595

[56] References Cited

U.S. PATENT DOCUMENTS

| | | | |
|---|---|---|---|
| 2,077,422 | 4/1937 | Lazier | 260/347.8 |
| 2,094,975 | 10/1937 | Adkins et al. | 252/467 X |
| 3,374,184 | 3/1968 | McEvoy et al. | 252/467 |

Primary Examiner—W. J. Shine
Attorney, Agent, or Firm—T. Gene Dillahunty; Vernon F. Venne; William Kammerer

[57] ABSTRACT

A copper chromite catalyst having improved activity is prepared by forming a basic copper ammonium chromate complex in a known manner. The complex is decomposed by sintering at temperatures near 300° C. to yield a copper chromite catalyst of improved activity. The copper chromite catalyst is especially useful in liquid phase production of furfuryl alcohol from furfural by hydrogenation. The hydrogenation reaction takes place at low pressure, e.g. under 30 atmospheres, due to the increased activity of the catalyst.

10 Claims, No Drawings

COPPER CHROMITE CATALYST FOR PREPARATION OF FURFURYL ALCOHOL FROM FURFURAL

BACKGROUND OF THE INVENTION

The present invention relates to an improved copper chromite catalyst which shows much greater activity in reducing an aldehyde to an alcohol than copper chromite catalysts known in the prior art. Specifically, the copper chromite catalyst of this invention allows the production of furfuryl alcohol at pressures which are much below those pressures for batch preparation of furfuryl alcohol of the prior art. The sintering temperature at which the copper chromite catalyst is formed, by decomposition of a copper ammonium chromite complex, is believed to be responsible for the increased activity of the catalyst.

It is known that a copper chromite catalyst may be prepared in the following manner. Copper sulfate, $CuSO_4.5H_2O$, and sodium dichromate, $Na_2Cr_2O_7.2H_2O$, can be combined with ammonium hydroxide to form a complex from which copper chromite may be prepared. The copper sulfate and sodium dichromate are dissolved in water to form a solution. To this solution ammonium hydroxide is added until the pH reaches 7.0 to 7.5. A precipitate is formed which is a complex and according to the literature has the formula $Cu(OH)NH_4CrO_4$. This complex is purified and used to prepare copper chromite. It is believed that the following equation represents the formation of the complex:

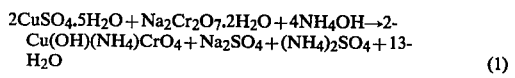

$$2CuSO_4.5H_2O + Na_2Cr_2O_7.2H_2O + 4NH_4OH \rightarrow 2Cu(OH)(NH_4)CrO_4 + Na_2SO_4 + (NH_4)_2SO_4 + 13H_2O \quad (1)$$

The production of copper chromite is carried out by decomposing the complex by heat. The formula for the decomposition reaction described by the prior art is as follows:

$$2Cu(OH)NH_4CrO_4 \rightarrow Cr_2O_3.2CuO + N_2 + 5H_2O \quad (2)$$

The above reaction (1) is known to be highly exothermic. The decomposition reaction begins when the temperature of the complex reaches approximately 230° C. Because of the exothermic nature of the reaction it is also self sustaining. It is known that if the temperature at which the decomposition reaction (2) occurs is allowed to reach a temperature of 400° or above that the copper chromite catalyst produced will have diminished activity and accordingly the decomposition reaction temperature was controlled so that the temperature at which the reaction (2) takes place is below 400° C. The prior art copper chromite catalysts formed as described typically have a low loss on ignition and a highly crystalline structure.

Copper chromite catalysts prepared as described above are known to be useful as catalysts for reducing aldehydes to alcohols in the presence of unsaturation. This knowledge has direct application to the production of furfuryl alcohol from furfural. The prior art teaches that the reduction of furfural to furfuryl by hydrogenation using a liquid phase process and using copper chromite as a catalyst will occur at 100 atmospheres and at temperatures of 200° C. or less. This process is said to give almost quantitative yields of furfuryl alcohol.

It is further known that calcium oxide, CaO, is useful in this reaction to improve the selectivity of the reaction. The use of calcium oxide is desirous since this compound prevents the formation of ethers. Ethers may be formed in this reaction after furfuryl alcohol is formed. Apparently calcium oxide is able to prevent the conversion of alcohol into ether and thus improves the selectivity of the preparation of furfuryl alcohol It appears that other metal oxides may also accomplish this function. It is not believed that the metallic oxides have any effect upon the reaction (3), catalytic or otherwise, other than the improvement of selectivity, but the mechanism is unknown.

It is desirable to improve the prior art liquid phase methods of preparing furfuryl alcohol from furfural. One disadvantage of the prior art is that high pressure, 100 atmospheres or more, is required.

Accordingly, it is an object of this invention to provide a catalyst which allows the liquid phase preparation of furfuryl alcohol from furfural at pressures lower than those of the prior art. The object described above is ideally reached without sacrificing the quantitative yield of furfuryl alcohol and without decreasing the rate of conversion at the catalyst levels of the prior art.

SUMMARY OF THE INVENTION

The abovementioned objectives have been accomplished by preparing a copper chromite catalyst essentially in the manner taught by the prior art. However, rather than carrying out the decomposition reaction at the temperatures taught by the prior art, i.e. below 400° C., the temperature of the decomposition reaction is much more strictly controlled and is carried out at around or below 300° C., and preferably at 275° C. plus or minus 5° C. The copper chromite catalyst obtained as described above allows the conversion of furfural to furfuryl alcohol to take place, using a batch or liquid phase method, at relatively low pressures—under 30 atmospheres—as compared to those pressures used in prior art. The operation of the reaction at the lower pressures—under 40 atmospheres—is safer and allows the use of much simplified and lower cost reactors. In addition the catalyst of this invention possesses such a degree of activity that the time required to convert furfural to furfuryl alcohol is at least as good, at comparable catalyst levels, as with prior art copper chromite catalysts. Further, the conversion of furfural to furfuryl is essentially 100% using the catalyst of this invention, i.e. very small amounts of by-products are formed.

DETAILED DESCRIPTION OF THE INVENTION

As stated above the critical feature of the preparation of the copper chromite catalyst which allows the production of furfuryl alcohol from furfural at pressures below 40 atmospheres is that the copper chromite catalyst is formed by decomposing a copper ammonium chromate complex at temperatures near or below 300° C. with a temperature of 275° C. plus or minus 5° C. seeming to be most desirable. Essentially the preparation of the copper chromite catalyst is carried out as taught by the prior art. That is to say, as shown in Equation (1), a precipitate is formed by the addition of ammonium hydroxide to the solution of sodium dichromate and copper sulfate. The precipitation is carried out by adding ammonium hydroxide to the solution until the pH of the combination reaches 7.0 to 7.5. At this point a complex is formed having the formula Cu- (OH)(NH$_4$)CrO$_4$. It is believed that other copper containing compounds may be used as well as copper sulfate and that other sources of chromium ions may be used as well as sodium dichromate. The ratio of moles of copper compound to moles of chromium compound may be varied. It is preferred to use a mole ratio of 2.0 moles copper sulfate to 1.0 moles sodium dichromate when these compounds are utilized.

The complex described above is purified by washing and drying and then heated by sintering or roasting to form the copper chromite catalyst. As stated previously it is critical that the sintering or roasting of the complex take place near or below 300° C. and preferably at 275° C. plus or minus 5° C. The decomposition reaction which occurs upon heating is highly exothermic and it is most important to assure that the temperature of the complex that is undergoing transformation to copper chromite is maintained near or below the desired temperature. In view of the self sustaining nature of the reaction this may require monitoring the temperature of the material. The copper chromite formed has a high surface area (eg. greater than 50 m$^2$/gram). It also appears to be a nearly purely amorphous material, that is to say there is essentially no crystalline structure present.

The reason for the improved activity of copper chromite catalyst prepared in the manner described above is not understood. However, it is quite clear that the temperature at which the complex is sintered or roasted, i.e., the temperature at which decomposition occurs, is the critical factor which leads to the improved activity. As shown by the examples set forth below it can be seen that the improved activity of the copper chromite catalyst, produced as described, results in dramatic and unexpected changes in the conditions used in the production of furfuryl alcohol from furfural when compared to the same reaction using copper chromite catalysts of the prior art.

The copper chromite catalyst of this invention is also characterized by a high loss on ignition—greater than 10%. Copper chromite catalysts of the prior art are not known to have as high a loss on ignition. The copper chromite catalyst of this invention is also stable. The catalyst can apparently be stored for months without loss of activity.

As has been previously stated, the copper chromite catalyst of this invention is especially useful in the liquid phase preparation of furfuryl alcohol from furfural by hydrogenation. The conversion is best accomplished using freshly distilled furfural. However, the catalyst of this invention also is useful in converting furfural, which has set for more than a week, into furfuryl. If the furfural is not fresh more catalyst may be required. This reaction of furfural to furfuryl alcohol which is well known, takes place as follows:

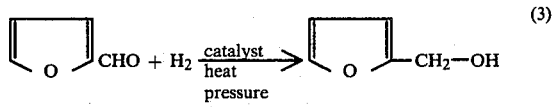
(3)

The conditions at which this reaction will take place using the copper chromite catalyst of this invention are 130° C. to 200° C. at pressures no greater than 30 atmospheres. The copper chromite catalyst is present in varying amounts depending upon the rate of reaction desired. On a commercial scale for efficient conversion of furfural to furfuryl it appears that the minimum effective amount of catalyst needed to be present to catalyze the reaction (3) is 0.30%. The copper chromite catalyst of this invention may be recycled after one batch of furfural is converted to furfuryl alcohol. It also appears that the copper chromite catalyst of this invention may be mixed with other known catalyst useful for reducing aldehydes to alcohols.

It is unadvisable to allow the reaction converting furfural into furfuryl alcohol to occur at temperatures above 200° C. Temperatures exceeding 200° C. will reduce the selectivity of the reaction, i.e., materials other than furfuryl alcohol will be produced. As previously mentioned, the use of calcium oxide or other metallic oxides is also advisable. These compounds serve to increase the selectivity of the reaction.

The invention is further illustrated by the following examples in which all parts and percentages are by weight unless otherwise indicated. These non-limiting examples are illustrative of certain embodiments designed to teach those skilled in the art how to practice the invention and represent the best mode presently known for carrying out the invention.

EXAMPLE 1

The copper chromite catalyst of this invention was prepared as follows. 500 grams of reagent grade copper sulfate, CuSO$_4$.5H$_2$O, and 298 grams of reagent grade sodium dichromate, NaCr$_2$O$_7$.2H$_2$O, were dissolved in 2.5 liters of deionized water. To this solution concentrated ammonium hydroxide—NH$_4$OH—was added. The ammonium hydroxide was added to the solution until the pH reached 7.2. A precipitate formed. After filtering the precipitate was washed until the wash water was a pale green in color. The reddish-brown precipitate was then dried in a forced-air oven for four hours in stainless-steel trays. The drying temperature was 95° C. to 100° C. The dried precipitate—a copper ammonium chromate complex—was crushed and screened to a size of approximately 200 mesh. The complex was placed in stainless-steel trays as a thin layer, approximately 4 to 6 millimeters in thickness. The trays were placed in a forced-air oven and heated. The oven temperature was held at 270° C. to 280° C. for three and one-half hours. Upon removal from the oven, the catalyst was observed to be a grayish black fluffy powder. Structural analysis revealed that the copper chromite catalyst was amorphous. The catalyst upon ignition lost 11.1 percent of its weight. The surface area of the catalyst was 55 m$^2$/gram. The catalyst is ready for use in reducing an aldehyde to an alcohol immediately upon removal from the oven.

EXAMPLE 2

The copper chromite catalyst of this invention was prepared as follows: A 25 gallon stainless-steel vessel, fitted with an agitator, was charged with 13.25 gallons of deionized water. Twenty pounds of reagent-grade copper sulfate, pentahydrate, and 11.2 pounds of sodium dichromate dihydrate were added to the vessel and stirred until they dissolved to form a solution. Concentrated ammonium hydroxide was added to this solution until a pH of 7.2 was obtained. A precipitate formed. The precipitate is a copper ammonium chromate complex. The precipitate was filtered and washed with deionized water. The washing is continued until the filtrate is a pale green. The precipitate formed is a reddish-brown solid after washing. The precipitate was dried overnight in a forced-air oven at 95° C. The precipitate was removed from the oven and crushed to a particle size less than 200 mesh. The particles were then placed in stainless-steel trays in layers less than 1 inch thick. Thermocouples were inserted inside the layer to monitor the temperature of the complex as it decomposed to form copper chromite catalyst. The complex was heated slowly in a forced-air oven. Upon reaching a temperature of 232°, the complex began to decompose and the temperature of the material rose rapidly. After the reaction was initiated the thermocouples indicated that during decomposition the temperature of the complex was sustained between 271° C. and 310° C., the 310° C. temperature in one area only. The exotherm was over within five minutes. The material was cooled to room temperature. The material was amorphous and demonstrated a loss on ignition of 11.0 percent. The surface area of the catalyst was 88 m$^2$/gram.

EXAMPLE 3

A copper chromite catalyst prepared as described in Example 1 was used to prepare furfuryl alcohol from furfural. In order to accomplish this, a 300 milliliter AE Magnadrive autoclave was thoroughly cleaned and dried. 200 grams of furfurl, 1.2 grams of a copper chromite catalyst prepared as described in Example 1 and 1.0 grams of calcium oxide were placed in the autoclave. The autoclave was sealed and purged twice with nitrogen and hydrogen. Hydrogen was added at a pressure of 350 psig. The autoclave was heated to 180° C. The reaction was monitored by GLC analysis. The furfural level fell below 0.5% after one and one-half hours. The hydrogen was turned off and the reactor cooled to below 100° C. The material in the autoclave was filtered to remove the catalyst. The material produced by this reaction was 98.6% furfuryl alcohol, the balance of the products being primarily unidentified impurities present in the furfural.

EXAMPLE 4

Furfuryl alcohol was produced using a batch or liquid phase process as follows. A 1-liter Parr autoclave was charged with 600 grams of furfural, 4.5 grams of a copper chromite catalyst prepared as described in Example 2, and 3.0 grams of calcium oxide. Prior to charging, the autoclave was thoroughly cleaned and dried. After charging, the reactor was sealed and purged twice with nitrogen and hydrogen. Hydrogen at 300 psig was then added to the autoclave. The autoclave was heated to 180° C. and the hydrogen pressure raised to 425 psig. Cooling was necessary to maintain the temperature at 180° C. The reaction upon completion, as shown by (1) GLC analysis, (2) cessation of hydrogen absorption and (3) falling temperature, was cooled to 80° C. The furfuryl alcohol produced was filtered to remove the catalyst. The reaction required 49 minutes. Conversion of furfural to furfuryl alcohol was greater than 99.9% with 99.6% selectivity.

EXAMPLE 5

A furfuryl alcohol was prepared by batch or liquid phase process as follows. A ten-gallon autoclave was carefully cleaned. Forty pounds of furfural, 109 grams of a copper chromite catalyst prepared as described in Example 1 and 2, and 91 grams of calcium oxide were charged into the autoclave. The autoclave was purged twice with nitrogen and hydrogen. Hydrogen was then added at 200 psig and the autoclave was heated. At 130° C. hydrogen began to be absorbed and the conversion of furfural to furfuryl alcohol began to take place. The hydrogen pressure was raised to 425 psig. The autoclave temperature was maintained at 180° C. Maintaining this temperature required cooling. After an hour and a half, the conversion of furfural to furfuryl alcohol was complete and analysis showed that 98.4% furfuryl alcohol was produced as an end product.

EXAMPLE 6

Furfuryl alcohol was prepared by using a commercially available copper chromite catalyst. This commercially available copper chromite catalyst was considered to be one of the best catalysts available for producing furfuryl alcohol from furfural using a batch or liquid phase hydrogenation process at low pressure. A 300 milliliter AE autoclave was thoroughly cleaned and dried. 200 grams of furfural, 3 grams of the commercially available copper chromite catalyst and 1 gram of calcium oxide were charged into the autoclave. The furfural (freshly distilled) was obtained from Profursa, a Spanish concern. The commercially available catalyst is sold by Girdler and is designated as G-22. Fisher technical calcium oxide was used. The autoclave was purged twice with nitrogen and hydrogen. Hydrogen was added to the autoclave. The hydrogen pressure was between 400 to 430 psig. The temperature of the autoclave was maintained at 180° C. After five hours, 99.8% of the furfural was converted to furfuryl alcohol. The selectivity was 98%.

EXAMPLE 7

Furfuryl alcohol was prepared from furfural using the copper chromite catalyst of this invention. The copper chromite catalyst used was prepared as described in Examples 1 and 2. The furfuryl alcohol was prepared in a 300 milliliter AE autoclave. The autoclave was thoroughly cleaned and dried. It was then charged with 200 grams of furfural, 1.5 grams of a copper chromite catalyst prepared as described in Examples 1 and 2, and 1 gram of calcium oxide. The furfural (freshly distilled) was obtained from Profursa, a Spanish concern. Fisher technical calcium oxide was used. The autoclave was pressurized to 400 to 430 psig with hydrogen. The temperature was raised and maintained at 180° C. After five and a third hours, 98.3% of the furfural was converted. The selectivity of the converted furfural to furfuryl alcohol was 98.8%.

Examination and comparison of Examples 6 and 7 demonstrate the increased activity resulting from the copper chromite catalyst of this invention. It will be noted that although all other conditions were essentially identical twice as much catalyst was required in Example 6, the prior art example, as was required in Example 7 in which the catalyst of this invention was used. Thus, it took twice as much prior art catalyst to accomplish the same results as are accomplished by the copper chromite catalyst of this invention.

What is claimed as this invention is:

1. A method of preparing a copper chromite catalyst comprising forming a basic copper ammonium chromate complex by precipitation by adding a hydroxide to a solution of a copper-containing salt and a chromium containing salt until the solution has a pH between 7 and 7.5, heating the complex formed until decomposition of the complex occurs and maintaining the decomposing complex at a temperature around or below 300° C. until decomposition is complete.

2. The method of claim 1 wherein the hydroxide is ammonium hydroxide.

3. The method of claim 1 wherein the copper salt is copper sulfate.

4. The method of claim 1 wherein the chromium salt is sodium dichromate.

5. A copper chromite catalyst prepared as a result of the process of claim 1.

6. A copper chromite catalyst comprising the product of decomposing by heating the complex until decomposition occurs and maintaining the temperature of the decomposing complex around or below 300° C. until decomposition is complete, said complex being a precipitate formed by adding ammonium hydroxide to a solution of copper sulfate and sodium dichromate until the pH of the solution is from 7.0 to 7.5.

7. The copper chromite catalyst of claim 5, said catalyst having a loss on ignition of 10% or more.

8. The copper chromite catalyst of claim 6, said catalyst having a loss on ignition of 10% or more.

9. The copper chromite catalyst of claim 5 wherein said catalyst has an essentially amorphous structure.

10. The copper chromite catalyst of claim 6 wherein said catalyst has an essentially amorphous structure.

* * * * *